United States Patent
Huertas Fernandez et al.

(10) Patent No.: US 12,280,257 B2
(45) Date of Patent: Apr. 22, 2025

(54) PRECISE TARGETING IN A SPINAL CORD STIMULATION SYSTEM

(71) Applicant: Boston Scientific Neuromodulation Corporation, Valencia, CA (US)

(72) Inventors: Ismael Huertas Fernandez, Seville (ES); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 438 days.

(21) Appl. No.: 17/663,503

(22) Filed: May 16, 2022

(65) Prior Publication Data

US 2022/0387808 A1    Dec. 8, 2022

Related U.S. Application Data

(60) Provisional application No. 63/195,899, filed on Jun. 2, 2021.

(51) Int. Cl.
*A61N 1/36* (2006.01)
*A61N 1/372* (2006.01)
*A61N 1/05* (2006.01)

(52) U.S. Cl.
CPC ..... *A61N 1/36132* (2013.01); *A61N 1/36071* (2013.01); *A61N 1/3615* (2013.01);
(Continued)

(58) Field of Classification Search
CPC ............ A61N 1/36132; A61N 1/36071; A61N 1/3615; A61N 1/36182; A61N 1/37241;
(Continued)

(56) References Cited

U.S. PATENT DOCUMENTS 6,308,102 B1 * 10/2001 Sieracki ............. A61N 1/36071
607/59
6,516,227 B1    2/2003 Meadows et al.
(Continued)

FOREIGN PATENT DOCUMENTS

| WO | 2009/137121 A1 | 11/2009 |
| WO | 2020/223165 | 11/2020 |
| WO | 2021/178105 | 9/2021 |

OTHER PUBLICATIONS

International Search Report and Written Opinion regarding corresponding PCT Application No. PCT/US2022/072343, mailed Aug. 31, 2022.

*Primary Examiner* — Eugene T Wu
(74) *Attorney, Agent, or Firm* — Lewis & Reese, PLLC

(57) ABSTRACT

Systems and methods are disclosed to permit a patient to use his external controller to move the location of stimulation in an implantable stimulator system. The external controller can be programmed with a steering algorithm, which prompts the patient to enter certain data regarding their symptoms (e.g., pain), such as pain scores and stimulation coverage. Such data is preferably entered for a plurality of different regions of the patient's body. The algorithm can compute for each body regions a targeting precision value (TP), and from these values determine a steering vector D that suggests a direction and/or a magnitude that stimulation can be moved in the electrode array to more precisely target the patient's pain. The patient may then move the location of the stimulation in accordance with the steering vector using their external controller. The algorithm can be repeated if necessary to again move the stimulation.

18 Claims, 9 Drawing Sheets

(52) U.S. Cl.
CPC ..... *A61N 1/36182* (2013.01); *A61N 1/37241* (2013.01); *A61N 1/37247* (2013.01); *A61N 1/0551* (2013.01)

(58) Field of Classification Search
CPC .............. A61N 1/37247; A61N 1/0551; A61N 1/36185
See application file for complete search history.

(56) References Cited

U.S. PATENT DOCUMENTS

| | | | |
|---|---|---|---|
| 6,622,048 B1 * | 9/2003 | Mann | A61N 1/36071 607/46 |
| 8,606,362 B2 | 12/2013 | He et al. | |
| 8,620,436 B2 | 12/2013 | Parramon et al. | |
| 8,644,947 B2 | 2/2014 | Zhu et al. | |
| 9,259,574 B2 | 2/2016 | Aghassian et al. | |
| 9,498,622 B2 | 11/2016 | King et al. | |
| 10,881,859 B2 | 1/2021 | Brill et al. | |
| 10,994,142 B2 | 5/2021 | Moffitt | |
| 2015/0080982 A1 | 3/2015 | Funderburk | |
| 2015/0231402 A1 | 8/2015 | Aghassian | |
| 2015/0360038 A1 | 12/2015 | Zottola et al. | |
| 2016/0144183 A1 | 5/2016 | Marnfeldt et al. | |
| 2016/0220179 A1 * | 8/2016 | Rigoard | G16H 40/63 |
| 2017/0209702 A1 | 7/2017 | Lee et al. | |
| 2018/0071513 A1 | 3/2018 | Weiss et al. | |
| 2018/0071520 A1 | 3/2018 | Weerakoon et al. | |
| 2019/0046800 A1 | 2/2019 | Doan et al. | |
| 2019/0083796 A1 | 3/2019 | Weerakoon et al. | |
| 2020/0147388 A1 | 5/2020 | Huertas Fernandez et al. | |
| 2020/0147397 A1 * | 5/2020 | Huertas Fernandez | A61N 1/36062 |
| 2020/0147400 A1 | 5/2020 | Moffitt et al. | |
| 2020/0222704 A1 | 7/2020 | Moffitt et al. | |
| 2020/0230410 A1 | 7/2020 | Zhang et al. | |
| 2020/0254256 A1 | 8/2020 | Moffitt et al. | |
| 2021/0008371 A1 * | 1/2021 | Annecchino | A61N 1/36071 |
| 2021/0196956 A1 | 7/2021 | Juarez Paz | |

\* cited by examiner

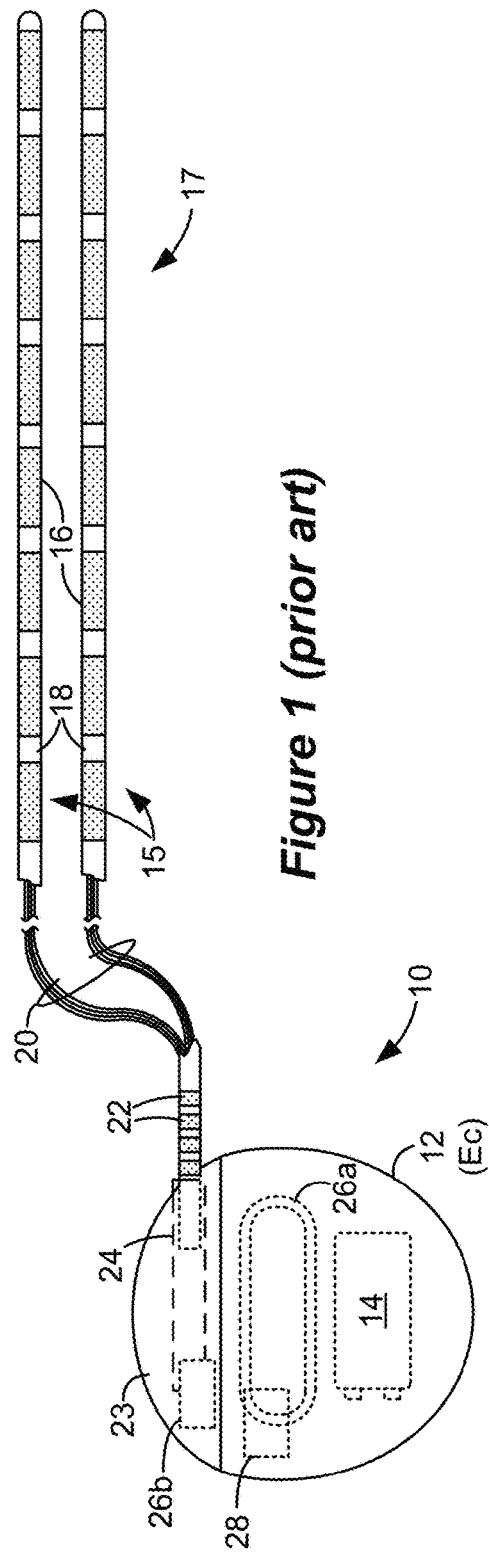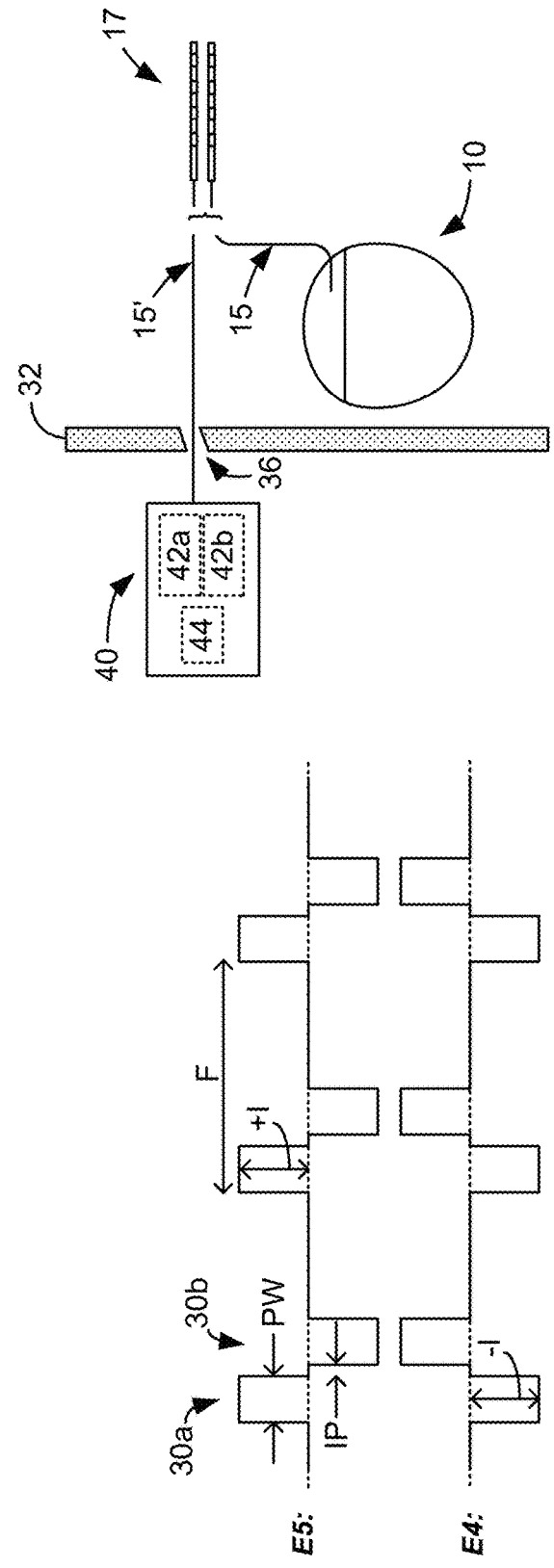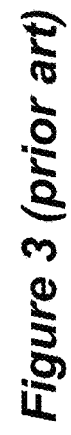

PRECISE TARGETING IN A SPINAL CORD STIMULATION SYSTEM

CROSS REFERENCE TO RELATED APPLICATIONS

This is a non-provisional application of U.S. Provisional Patent Application Ser. No. 63/195,899, filed Jun. 2, 2021, which is incorporated herein by reference, and to which priority is claimed.

FIELD OF THE INVENTION

This application relates to Implantable Medical Devices (IMDs) generally, Spinal Cord Stimulators more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. Lead 15 can also comprise a paddle lead, which includes a matrix of electrodes 16 (electrode array 17) on one of the paddle's surfaces, as is well known. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG 10 may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (I; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode (during first phase 30a), and thus provides pulses which source a positive current of amplitude +I to the tissue. Electrode E4 has been selected as a cathode (during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time.

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b.

IPG 10 includes stimulation circuitry 28 that can be programmed to produce the stimulation pulses at the electrodes as defined by the stimulation program. Stimulation circuitry 28 can for example comprise the circuitry described in U.S. Patent Application Publications 2018/0071513 and 2018/0071520, or described in U.S. Pat. Nos. 8,606,362 and 8,620,436. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted as an electrode array 17 in the patient's tissue 32 at a target location, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a hand-held and portable patient external controller 45, and a clinician programmer 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40. If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters can be defined for a stimulation program. Values for stimulation parameters relating to the shape of the waveform (I; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92 or elsewhere in the GUI 64. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication.

In FIG. 5, the anodic current (+I) is shared between electrodes E5 and E13 (X=30% and 70% respectively), which positions an anode pole (+) at a location between these electrodes. This anode pole is sometimes referred to as a virtual pole because its position doesn't correspond to a physical position of one of the electrodes 16, as explained further in U.S. Pat. No. 10,881,859, which is incorporated by reference in its entirety. Likewise, the cathodic current (−I) is shared between electrodes E3 and E11 (X=30 and 70% respectively), which positions a (virtual) cathode pole (−) as shown. Together, the poles comprise a pole configuration 21, which in this case is a bipole. Other pole configurations could be used as well (e.g., tripoles). The pole configuration 21 establishes an electric field in the tissue, yet can still be defined as being at a particular location L1 in the electrode array 17. The location of a pole configuration 21 can be defined in different ways, but in the illustrated example the location L1 is defined at a point (x, y) in the electrode array 17 centered between the anode and cathode poles, which generally corresponds to the center (or centroid) of the produced electric field.

The cursor 94 can be used to position the pole configuration 21, or either of the poles individually. In this regard, an electrode configuration algorithm (not shown) can operate to automatically select certain electrodes, their polarities, and their relative percentages X % as necessary to position the poles at the depicted locations. The electrode configuration algorithm would comprise part of clinician programmer software 66 (FIG. 4), as is explained further in the above-incorporated '859 patent. The pole configuration 21, or any of the individual poles, can also be moved in the electrode array 17 using aspects of the GUI 64, such as directional arrows 85, or the joystick 58 (FIG. 4).

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +I and −I). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (I), etc. A mode menu 90 allows the clinician to choose different modes for determining stimulation parameters.

While GUI 64 is shown as operating in the clinician programmer 50, the user interface of the external controller 45 may provide similar functionality.

SUMMARY

A system is disclosed, which may comprise: an external device for communicating with a stimulator device having a plurality of electrodes forming an electrode array, the external device comprising: a user interface; and controller circuitry programmed with an algorithm, wherein the algorithm is configured to: program the stimulation device to provide stimulation at a first location in the electrode array; receive from the user interface a plurality of inputs for each of a plurality of body regions, wherein the plurality of inputs are indicative of how well the stimulation at the first location is targeting the patient's symptoms; compute a value for each of the body regions using the plurality of inputs for each body region; determine using the values at least a direction from the first location in which the stimulation can be moved in the electrode array to better target the patient's symptoms; and program the stimulator device to move the stimulation to a second location in the electrode array in accordance with the direction.

In one example, the controller circuitry is configured to program the stimulator device to move the stimulation upon receiving a selection from the user interface. In one example, the external device comprises a hand-held portable patient external controller. In one example, the plurality of inputs for each of the body regions comprise a pain score and an indication of stimulation coverage. In one example, the value for each of the body regions is computed using a model stored in the controller circuitry having the pain score and the indication of stimulation coverage as inputs. In one example, the controller circuitry is configured to determine using the values the direction and a distance from the first location in which the stimulation can be moved. In one example, the controller circuitry is configured to program the stimulator device to move the stimulation in the electrode array in accordance with the direction and the distance. In one example, the direction is determined by computing a gradient of the values over x and y dimensions. In one example, the direction is determined in accordance with a highest computed gradient. In one example, the controller circuitry is further configured to receive an adjustment to at least one stimulation parameter of the stimulation after it is moved to the second location. In one example, the at least one stimulation parameter comprises an amplitude of the stimulation. In one example, the at least one stimulation parameter is adjusted in accordance with the values. In one example, the at least one stimulation parameter is adjusted in accordance with one or more of an average of the values or a deviation of the values. In one example, the at least one stimulation parameter is adjusted to increase a neural dose of the stimulation if the average of the values or the deviation of the values is high, or wherein the at least one stimulation parameter is adjusted to decrease the neural dose of the stimulation if the average of the values or the deviation of the values is low.

A method is disclosed implementable using an external device in communication with a stimulator device having a plurality of electrodes forming an electrode array. The method may comprise: providing stimulation at a first location in the electrode array; receiving at a user interface of the external device a plurality of inputs for each of a plurality of body regions, wherein the plurality of inputs are indicative of how well the stimulation at the first location is targeting the patient's symptoms; computing a value for each of the body regions using the plurality of inputs for each body region; determining using the values at least a direction from the first location in which the stimulation can be moved in the electrode array to better target the patient's symptoms; and programming the stimulator device to move the stimulation to a second location in the electrode array in accordance with the direction.

In one example, the value for each of the body regions is computed using the external device. In one example, the at least the direction is determined using the external device. In one example, the stimulator device is programmed to move the stimulation using the user interface of the external device. In one example, the external device comprises a hand-held portable patient external controller. In one example, the plurality of inputs for each of the body regions comprise a pain score and an indication of stimulation coverage. In one example, the value for each of the body regions is computed using a model having the pain score and the indication of stimulation coverage as inputs. In one example, a direction and distance from the first location in which the stimulation can be moved is determined using the values. In one example, the stimulator device is programmed to move the stimulation in the electrode array in accordance with the direction and the distance. In one example, the direction is determined by computing a gradient of the values over x and y dimensions. In one example, the direction is determined in accordance with a highest computed gradient. In one example, the method further comprises adjusting at least one stimulation parameter of the stimulation after it is moved to the second location. In one example, the at least one stimulation parameter comprises an amplitude of the stimulation. In one example, the at least one stimulation parameter is adjusted in accordance with the values. In one example, the at least one stimulation parameter is adjusted in accordance with one or more of an average of the values or a deviation of the values. In one example, the at least one stimulation parameter is adjusted to increase a neural dose of the stimulation if the average of the values or the deviation of the values is high, or wherein the at least one stimulation parameter is adjusted to decrease the neural dose of the stimulation if the average of the values or the deviation of the values is low.

A non-transitory computer readable medium is disclosed comprising instructions executable on an external device for controlling a stimulator device that provides stimulation to a patient, wherein the instructions when executed enable the external device to: program the stimulation device to provide stimulation at a first location in the electrode array; receive from the user interface a plurality of inputs for each of a plurality of body regions, wherein the plurality of inputs are indicative of how well the stimulation at the first location is targeting the patient's symptoms; compute a value for each of the body regions using the plurality of inputs for each body region; determine using the values at least a direction from the first location in which the stimulation can be moved in the electrode array to better target the patient's symptoms; and program the stimulator device to move the stimulation to a second location in the electrode array in accordance with the direction.

BRIEF DESCRIPTION OF THE DRAWINGS

FIG. 1 shows an Implantable Pulse Generator (IPG) useable for Spinal Cord Stimulation (SCS), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

DETAILED DESCRIPTION

A significant issue in stimulation therapy, and Spinal Cord Stimulation (SCS) therapy in particular, is determining the stimulation parameters that are best able to treat a patient's symptoms. As noted above, SCS stimulation parameters can include features like the amplitude of stimulation (I), the pulse width (PW) of the stimulation pulses, and the frequency (F) at which the stimulation pulses are issued. Other stimulation parameters used to place the stimulation at a location (e.g., L1) in the electrode array 17 to best treat the patient's symptoms are also important, and can include the electrodes that are active to form the stimulation (E), the polarity (P) of those active electrodes, and a percentage (X) indicating a relative amount of the amplitude each active electrode should receive. As explained above, these parameters define the location of poles in the electrode array 17, and hence the location of the pole configuration 21.

The clinician programmer 50 is typically used to set these stimulation parameters for a patient, at least initially. Thereafter, a patient using his patient external controller 45 may also adjust at least some of the stimulation parameters, although perhaps not all of them. At a minimum, the external controller 45 usually permits the patient to adjust the amplitude (I) of the stimulation. This is sensible, because the stimulation may need to be changed depending on what the patient is doing. Patient activities (e.g., running, sleeping, etc.) and postures (e.g., standing, supine, prone, etc.) can affect the effectiveness of the stimulation therapy. For example, if a particular activity or posture moves the electrodes further from the spinal cord, it may be reasonable to increase the amplitude of the stimulation. Similarly, if a particular activity or posture moves the electrodes closer to the spinal cord, it may be reasonable to decrease the amplitude of the stimulation. Adjusting the amplitude can also be reasonable for other reasons. For example, the passage of time can cause changes in the electrical environment of the IPG (e.g., the formation of scar tissue or other factor that affect the coupling of the electrodes to the tissue). For these reasons, it is useful to allow the patient to adjust the amplitude to counteract these effects and to restore stimulation therapy to an effective level.

Figure 5:
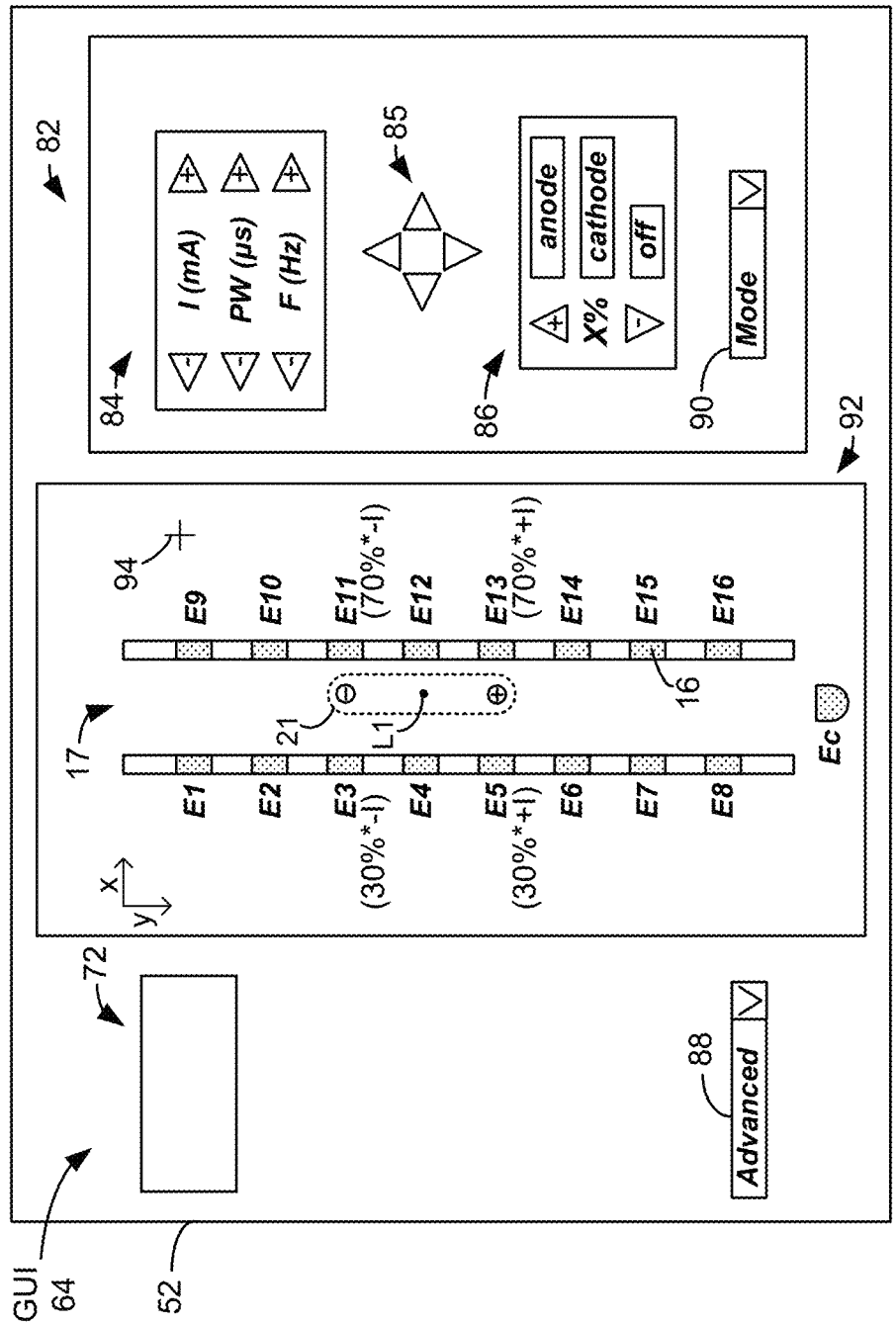
FIG. 5 shows a Graphical User Interface (GUI) of a clinician programmer external device for setting or adjusting stimulation parameters, in accordance with the prior art.

However, over time the patient may need other adjustments to therapy beyond amplitude adjustments. For example, the leads 15 comprising the electrode array 17 may move or migrate within the patient's spinal column. This means that stimulation provided at a particular location in the electrode array 17 (such as L1, FIG. 5) may become less effective over time because such stimulation is no longer being provided to the same neural tissue. This is unfortunate, because while the location of stimulation in the electrode array 17 can be moved as explained earlier, the patient typically lacks the tools to do so, because traditional patient external controllers 45 lack the ability to move the location of stimulation. Even if a patient external controller 45 has such functionality, it may be difficult for the patient to know how to move the stimulation in the electrode array: should it be moved up or down, or left or right, and by how much? Given the complexities involved in readjusting stimulation to recapture therapeutic efficacy, and in particular in moving the location of stimulation, a patient requiring such adjustment will typically need to present to the clinician to make such adjustments. This is burdensome on the patient, and is especially burden on the clinician, whose time will be increasingly spent on recalibrating stimulation for previously-implanted patients. This leaves less time for the clinician to tend newly-implanted patients who may need more significant or more immediate intervention.

To address this issue, the inventors disclose systems and methods to ease adjustment to a patient's stimulation. In particular, the disclosed approach provides an informed manner in which simulation can be adjusted, and in particular how stimulation can be moved in the electrode array 17. The approach can be implemented using a steering algorithm 200 (FIG. 6), which can be implemented using the clinician programmer 50, but which is most preferably performed using the patient external controller 45. This allows patients to make stimulation adjustments to therapy themselves, and without the need of clinician assistance.

The steering algorithm 200 prompts the patient to enter certain data regarding their symptoms (e.g., pain), and preferably such data includes both pain scores (S) and information relating to how well stimulation is covering or overlapping the patient's pain (C). Such data is preferably entered for a plurality of body regions, as explained further below. The algorithm 200 can then compute for each body regions a targeting precision value (TP) using the pain scores and coverage data S and C. These targeting precision values can then be translated to a targeting precision (TP) map 132, which maps the TP values to (x,y) coordinates in the patient's tissue and/or the electrode array 17. The algorithm 200 can determine a steering vector D from the TP map 132. Preferably this vector D suggests a direction in which the patient's stimulation can be moved in the electrode array 17 to more precisely target the patient's pain, and vector D may further also specify a distance for such movement. The patient may move the location of the stimulation on their external controller 45 in accordance with the steering vector D, or the algorithm 200 may move the stimulation automatically. The algorithm 200 can be repeated if necessary to allow for the input of new pain information and to move the simulation again to see if therapeutic effectiveness can be further improved. After the stimulation is moved, the patient may adjust various stimulation parameters (e.g., amplitude) as necessary. Furthermore, the steering algorithm 200 may suggest changes to the neural dose of stimulation (as affected by amplitude, pulse width, and/or frequency) that the patient should receive, and this determination can be made upon assessment of the TP values determined earlier.

Notice that the steering algorithm 200 as described relies on patient feedback regarding their symptoms, as ultimately reflected in the computed TP values. From these values, the algorithm 200 can suggest how stimulation should be moved and/or otherwise adjusted, which the patient can do using his external controller 45. The algorithm 200 takes guesswork away from patients when trying to determine a new location for stimulation, and allows patients to steer the stimulation in the electrode array 17 by themselves without clinician intervention.

Figure 6:
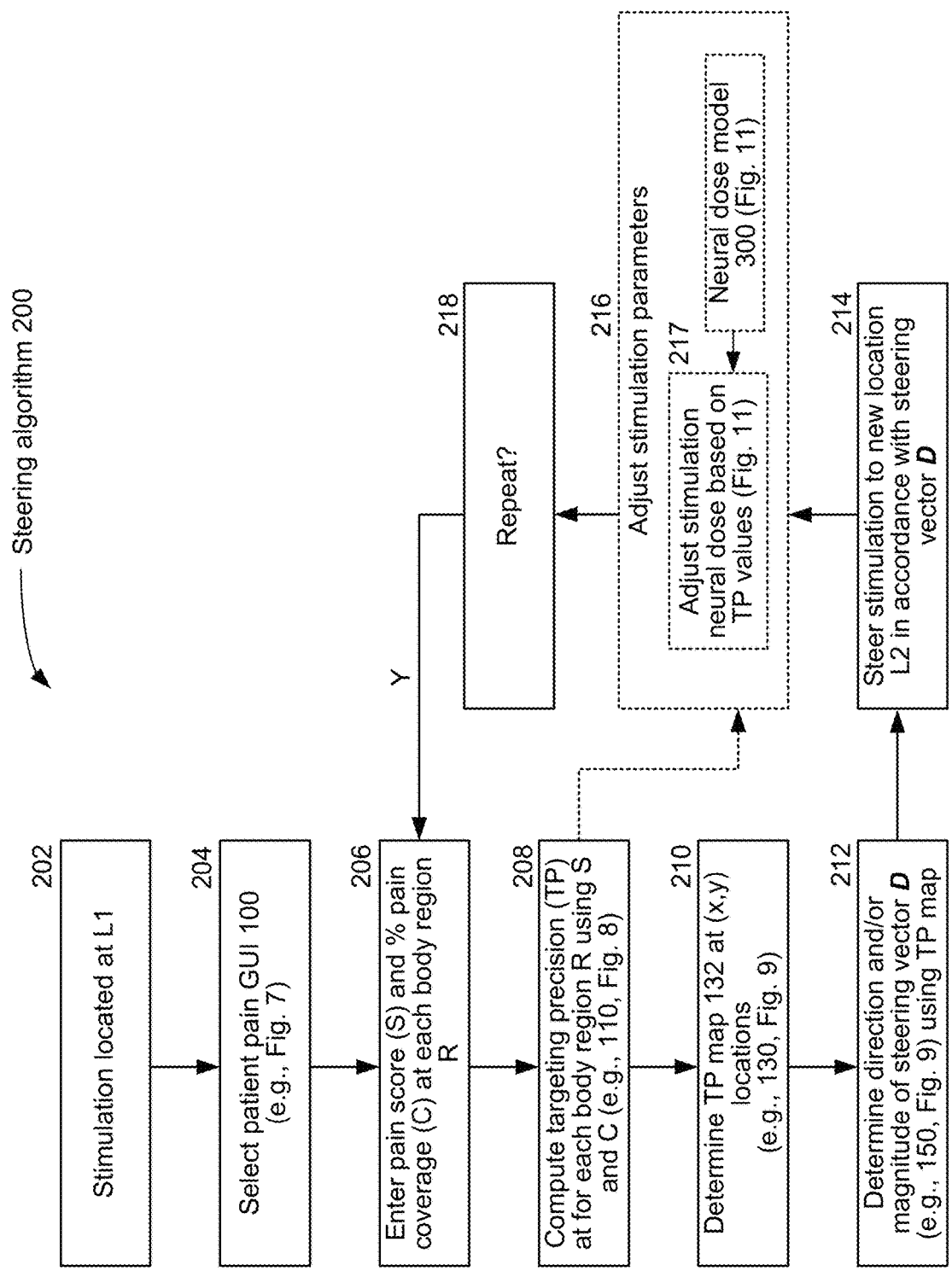
FIG. 6 shows an example of a steering algorithm implementable with an external device for controlling an IPG or ETS, which receives inputs from the patient, and determines a steering vector for moving stimulation in the patient's electrode array.

Explanation of steps in the steering algorithm 200 are shown in FIG. 6, with details shown in subsequent figures. Not all steps are necessary, and additional steps could be added in a different implementation. It is assumed here that steering algorithm 200 operates using the patient external controller 45, thus allowing a patient to adjust stimulation through use of the algorithm without clinician assistance. However, the algorithm 200 could also be used by a clinician using the clinician programmer 50. Aspects of the steering algorithm 200 can be programmed as software/firmware in the control circuitry of the external device being used, as explained further below.

The algorithm starts at step 202 with stimulation already reasonably established for the patient. For example, stimulation parameters such as amplitude, pulse width and the like have been previously determined. At step 202 it is also assumed that the stimulation has been initially established at a location L1 in the electrode array 17.

Figure 7:
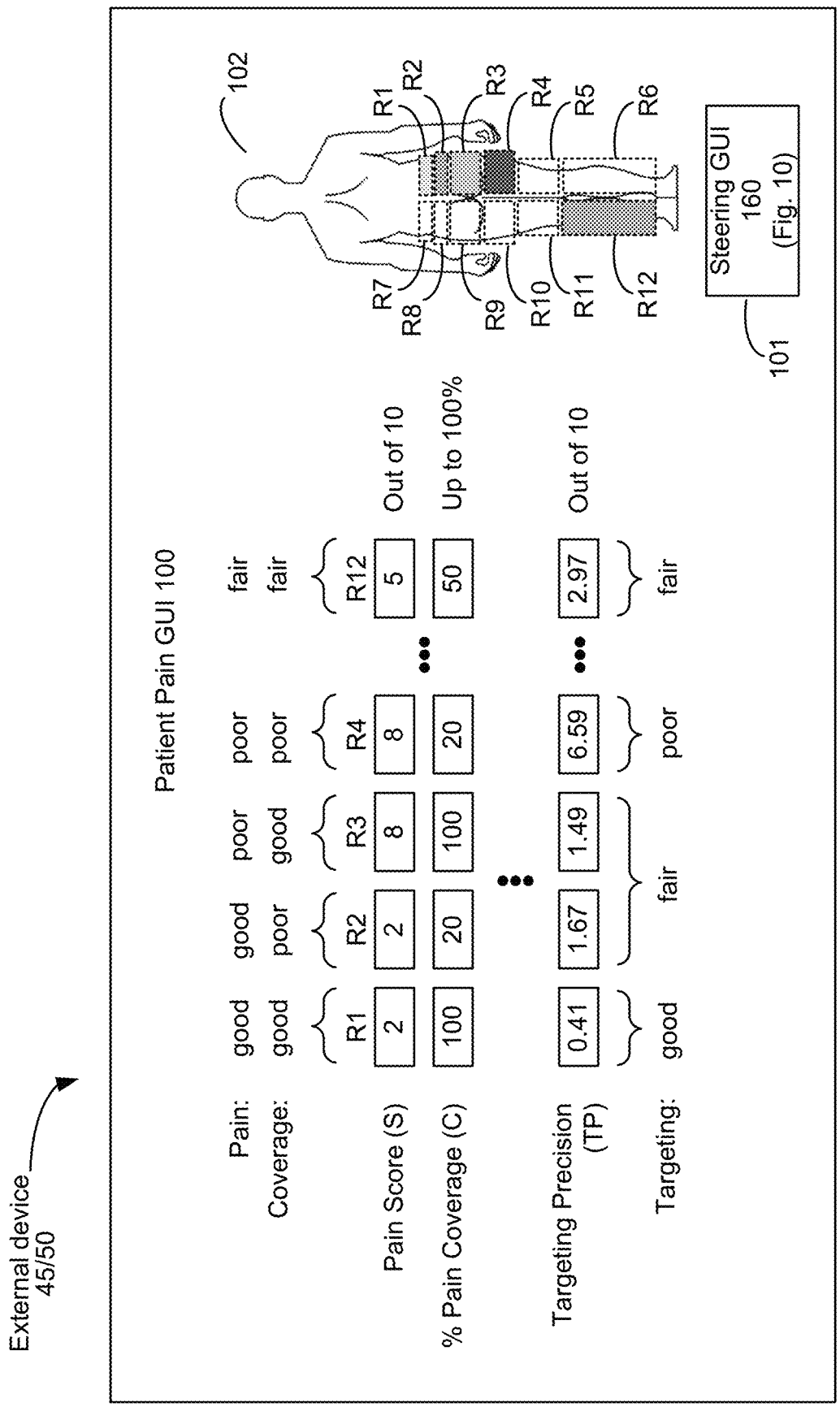
FIG. 7 shows a patient pain GUI used by the algorithm to receive the inputs from the patient, including pain scores and percentage coverage ratings for a plurality of body regions.

At step 204, the patient accesses an option in the user interface of the external controller 45 to bring up a patient pain GUI 100, which is shown in one example in FIG. 7. As shown, the patient pain GUI 100 allows the patient to enter certain inputs indicative of how well the stimulation is targeting the patient's symptoms at the current location (e.g., L1) in the electrode array. In particular (step 206), the patient is prompted to enter a pain score (S), which in this example comprise a NRS pain score, in which 0 suggests no pain and 10 extreme pain. The patient is also prompted to enter information relating to how well stimulation is covering the patient's pain (C). Especially if the patient is able to feel the stimulation (paresthesia), the patient can quantify a percentage denoting how well the paresthesia is covering or overlapping their pain, from 0% denoting no coverage to 100% denoting complete coverage. As shown in FIG. 7, these values are entered by the patient at a plurality of body regions Ri. A body graphic 102 is provided in the GUI 100 showing the locations of the different body regions. For example, regions R1-R6 appear on the right side of the patient's body at progressively lower body positions (e.g., from the right middle of the back down to the right lower leg). Regions R7-R12 are similar although appearing on the patient's left side. These body regions are merely examples, and different regions could be denoted for use in the algorithm 200. For example, the body regions may be bigger or smaller, and can comprise pixels or voxels. Body region definition can also be based on different criteria, such as dermatomes or other established criteria, such as a CHOIR body map.

Figure 4:
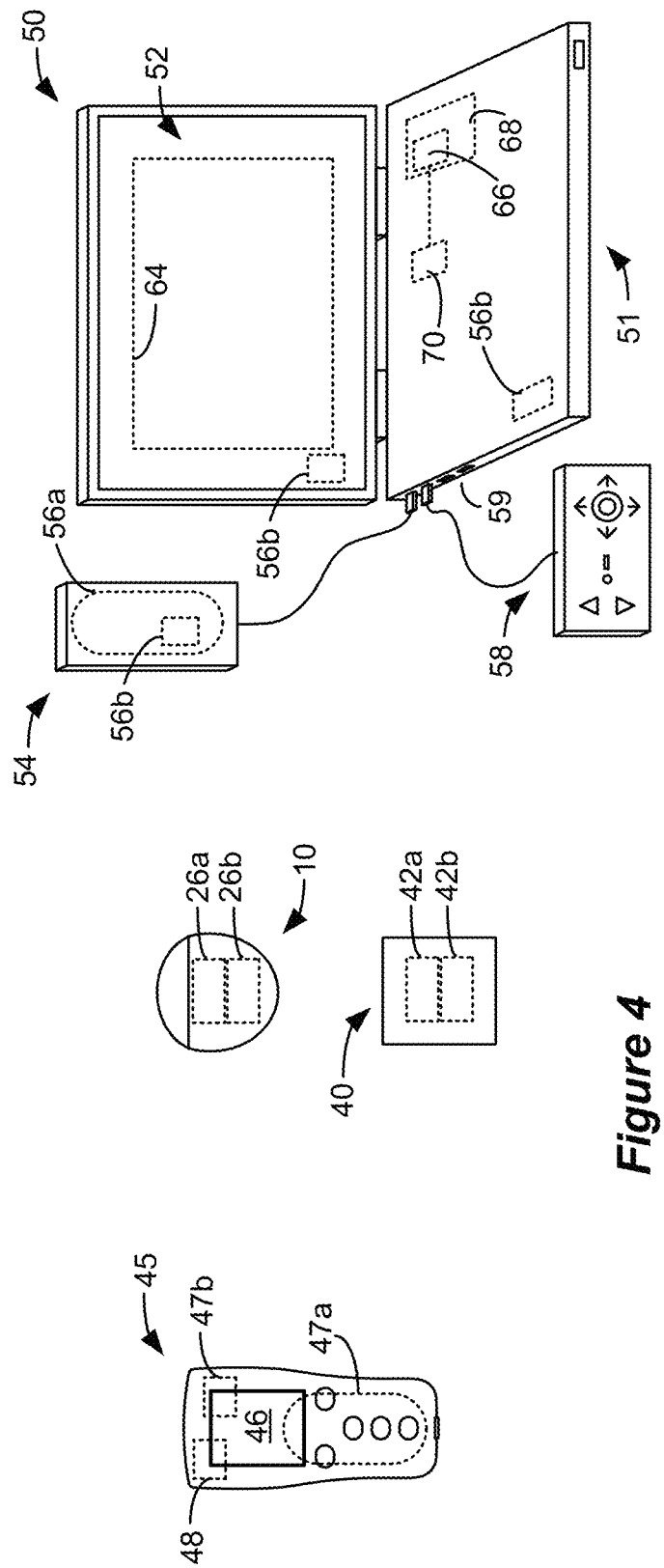
FIG. 4 shows various external devices capable of communicating with and programming stimulation in an IPG and ETS, in accordance with the prior art.
Figure 8:
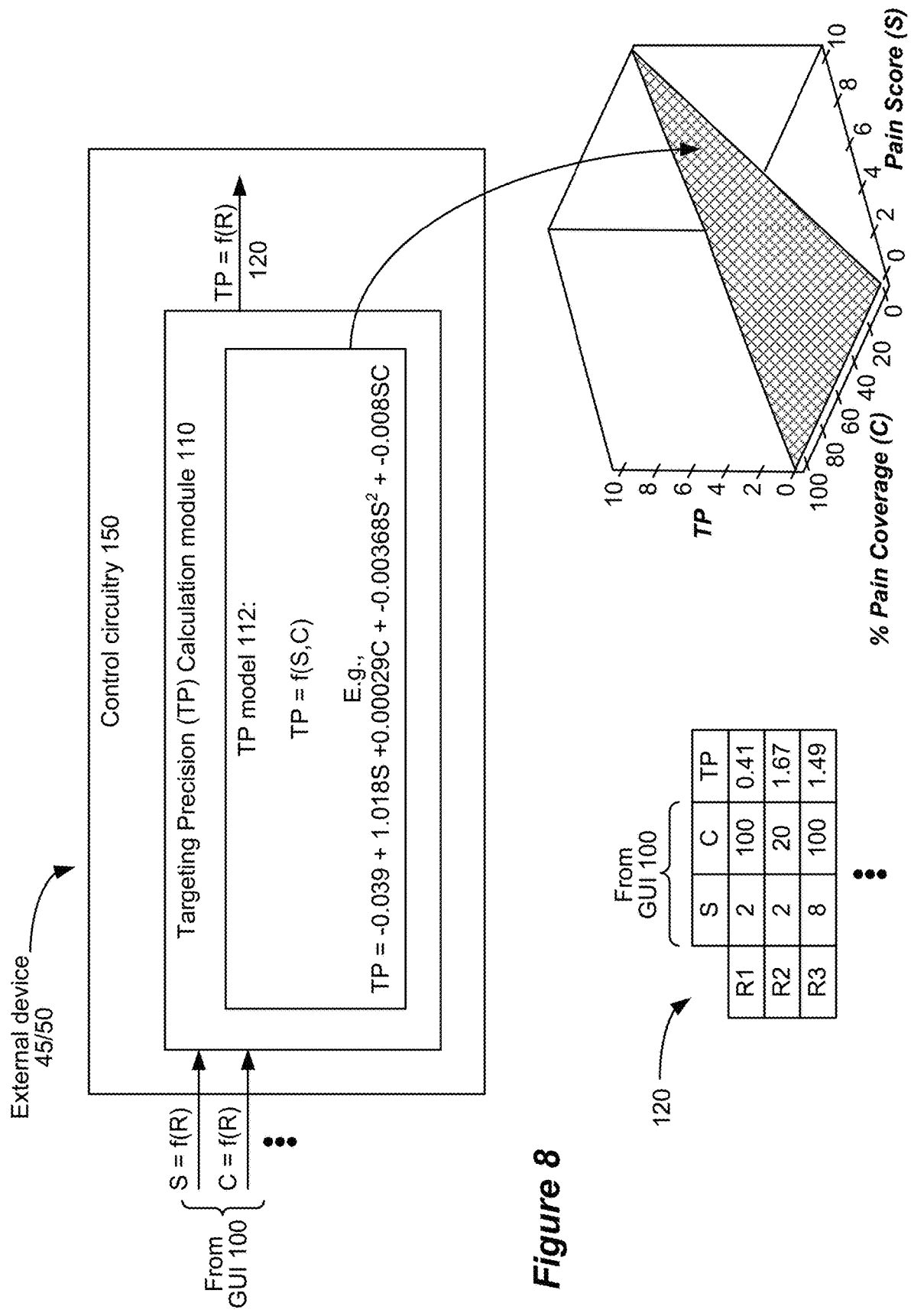
FIG. 8 shows control circuitry in the external device, including a programmed targeting precision calculation module for computing targeting precision (TP) values at each of the body regions using the patient inputs.

At step 208, the algorithm 200 computes a targeting precision (TP) value at each of the body regions R using at least the pain score S and percentage coverage C for each body region. It is preferred to use at least these two inputs S and C when computing TP values because the resulting value is indicative of a precision with which the stimulation is targeting the patient's pain in each body region, as explained further below. FIG. 8 shows the control circuitry 150 involved in implementing the steering algorithm 200, and shows programming of a software/firmware module 110 useful for calculating the TP values. (Here, the control circuitry 150 can represent either the control circuitry 48 of the external controller 45 or the control circuitry 70 of the clinician programmer 50 (FIG. 4), depending on which of these external devices are used). As shown, the module 110 receives the S and C values for each body region R. Included within module 110 is a target precision model 112 for determine the TP values at each body region R. In the example shown, the TP values are calculated using a polynomial expression dependent on S and C. The terms and coefficients used in TP model 112 could vary depending on designer preferences, but here the terms and coefficients have been chosen to yield TP values that range approximately from 0 (precise targeting) to 10 (poor targeting). As, the TP values are made similar to the pain scores S, which also can range from 0 (good) to 10 (poor). TP values calculated by the TP model 112 at different S and C values are shown graphically at the bottom right of FIG. 8. Also shown in FIG. 8 is a TP data set 120 that stores the computed TP values for each body region R1.

The calculated TP values are also shown in the patient pain GUI 100 in FIG. 7. In this example, it is assumed that each body region R has different pain scores S and percentage coverages C. For example, for body region R1, the pain score is good (S=2) and so is the coverage (C=100). This means the stimulation provided by the patient's IPG (or ETS) precisely targets pain within region R1, and thus the TP value calculated for this region is good (i.e., low, 0.41). For body region R2, the pain score is good (S=2), but the coverage is poor (C=20). In this sense, the stimulation precision is somewhat lacking for region R2: pain is minimized, but the stimulation also doesn't seem to affect this region much. As a result, the resulting TP value is higher (1.67), and fair (although not necessarily good). For body region R3, the pain score is poor (S=8), but the coverage is good (C=100). Again, the stimulation precision is somewhat lacking for region R3: the stimulation affects the region, but doesn't well treat the pain, and as a result, the resulting TP value is higher (1.49), and fair. For body region R4, the pain score is poor (S=8), and the coverage is poor (C=20), and this lack of precision is reflected in the resulting high (poor) TP value (6.59). For body region R12, the pain score is fair (S=5), and the coverage is also fair (C=50), which results in a fair TP value (2.97). Note that the computed TP values can be displayed on the body graphic 102 with different colors or shading to highlight their relative differences. For example, in FIG. 7, darker shaded regions are indicative of higher (worse) TP values and hence highlight body regions that are not precisely targeted by the stimulation.

Figure 9:
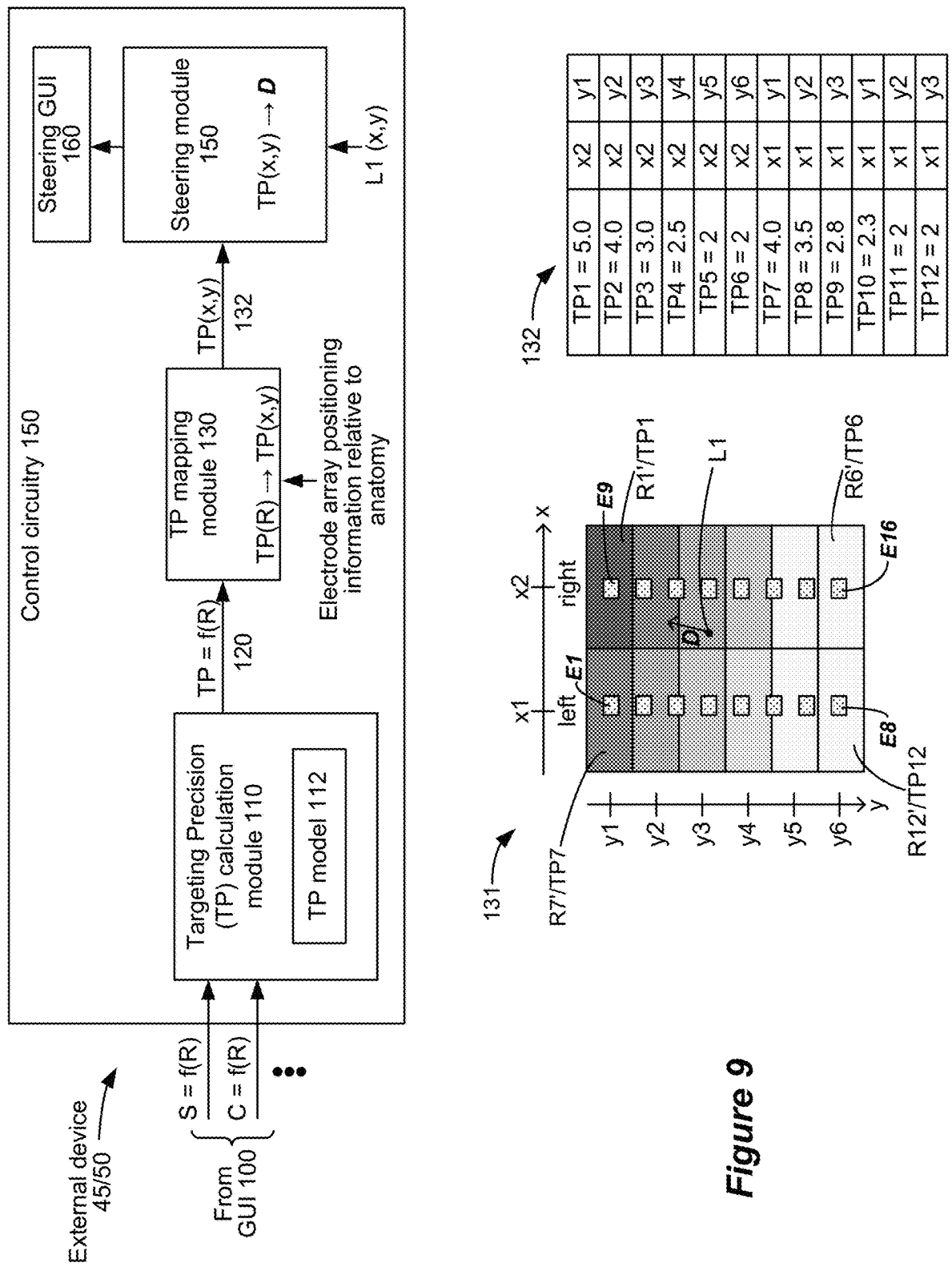
FIG. 9 shows further programmed modules in the control circuitry, including a targeting precision mapping module and a steering module, for determining from the TP values a steering vector D which suggests how to move the stimulation in the electrode array to better target the patient's pain.

At step 210, the steering algorithm 200 determines a targeting precision (TP) map 132, which is shown in FIG. 9, and which can be formed using a TP mapping module 130 programmed into the control circuitry 150. The TP map 132 comprises the TP values mapped to (x,y) dimensions in the electrode array 17 and/or the patient's spinal neural tissue recruited by the electrode array. Mapping of the TP values to (x,y) positions is assisted by understanding spinal neural tissue that innervates the body regions Ri, and graphic 131 is useful in this regard. Graphic 131 shows spinal neural tissue in relation to the electrode array 17 implanted in the patient. The spinal neural tissue is broken down into spinal neural regions Ri', each of which innervates a different one of the body regions Ri. It is generally known where a particular spinal neural region Ri' exists in a patient's spinal cord. For example, it may be known that body region R1 is innervated by spinal neural region R1' that exists between vertebrae T8 and T9 for example.

Just as the spinal neural regions Ri' may be defined with reference to anatomy, so to can the positions of the electrodes 16 in electrode array 17 be defined with reference to anatomy. For example, it may be known that the electrode array 17 is placed between certain vertebrae, such as from T8 to T11. From this, the position of individual electrodes 16 relative to the patient's anatomy may be determined. For example, it may be known that electrode E9 is positioned between vertebrae T8 and T9 for example. Positioning information of the electrode array 17 relative to the patient's anatomy may also be known using imaging technology, such as the use of fluoroscopy. Such positioning information of the electrode array 17 and/or individual electrodes 16 with reference to the patient's anatomy is provided to the TP mapping module 130 as shown.

Because each electrode 16's position relative to anatomy is known; the position of each spinal neural region Ri' is known; and the (x,y) position of the electrodes 16 is known in the electrode array 17, the mapping module 130 can determine the (x,y) position of the spinal neural regions Ri'. Further, these (x,y) positions of the spinal neural regions Ri' can be associated with the TP values of the body regions Ri they innervate. In short, this allows the TP mapping module 130 to determine (x,y) positions for each of the TP values computed earlier, as shown in TP map 132 in FIG. 9.

At step 212, the steering algorithm 200 can determine a steering vector D using TP map 132, and this occurs in steering module 150 shown in FIG. 9. The steering module 150 receives as an input the current (x,y) location L1 of the stimulation in the electrode array 17, and seeks to define steering vector D as an offset from this location. The steering algorithm 150 preferably defines steering vector D at least by a direction in which stimulation can be moved in the electrode array 17 to better recruit spinal neural tissue that is currently not being precisely targeted. Because in the depicted example TP values with higher values are not well targeted, operation of the steering module 150 tends to define vector D in a direction with higher TP values (i.e., towards darker shaded spinal neural regions Ri' in the graphic 131 of FIG. 9). Preferably, the steering module 150 will also define a magnitude (length) for vector D as well.

Steering module 150 can operate in different ways to determine steering vector D. For example, the steering module 150 can view the TP values as a two-dimensional surface, and can suggest a vector D that moves in a directional with the highest gradient (first spatial derivative) in the surface from the current stimulation location L1. The steering module 150 could also simply define vector D to point to the (x,y) location in TP map 132 that has the worst (highest) TP value. Because operation of the steering algorithm 200 can be iterative, as discussed further below, it is not crucial that the steering module 150 define the steering vector D perfectly. Instead, vector D may only seek to incrementally improve the precision of stimulation for the patient.

Note that while it is preferred for accuracy that the steering module 150 consider TP map 132 as disclosed, it is not necessary that the steering module receive electrode-array (x,y) positioning information that the map preferably provides. Instead, the steering module 150 may be able to determine steering vector D from knowledge of the position of the various body regions and their TP values. In short, the (x,y) positions in TP map 132 may be indicative of the position of body regions, and may not necessarily comprise (x,y) values in the electrode array 17.

Figure 10:
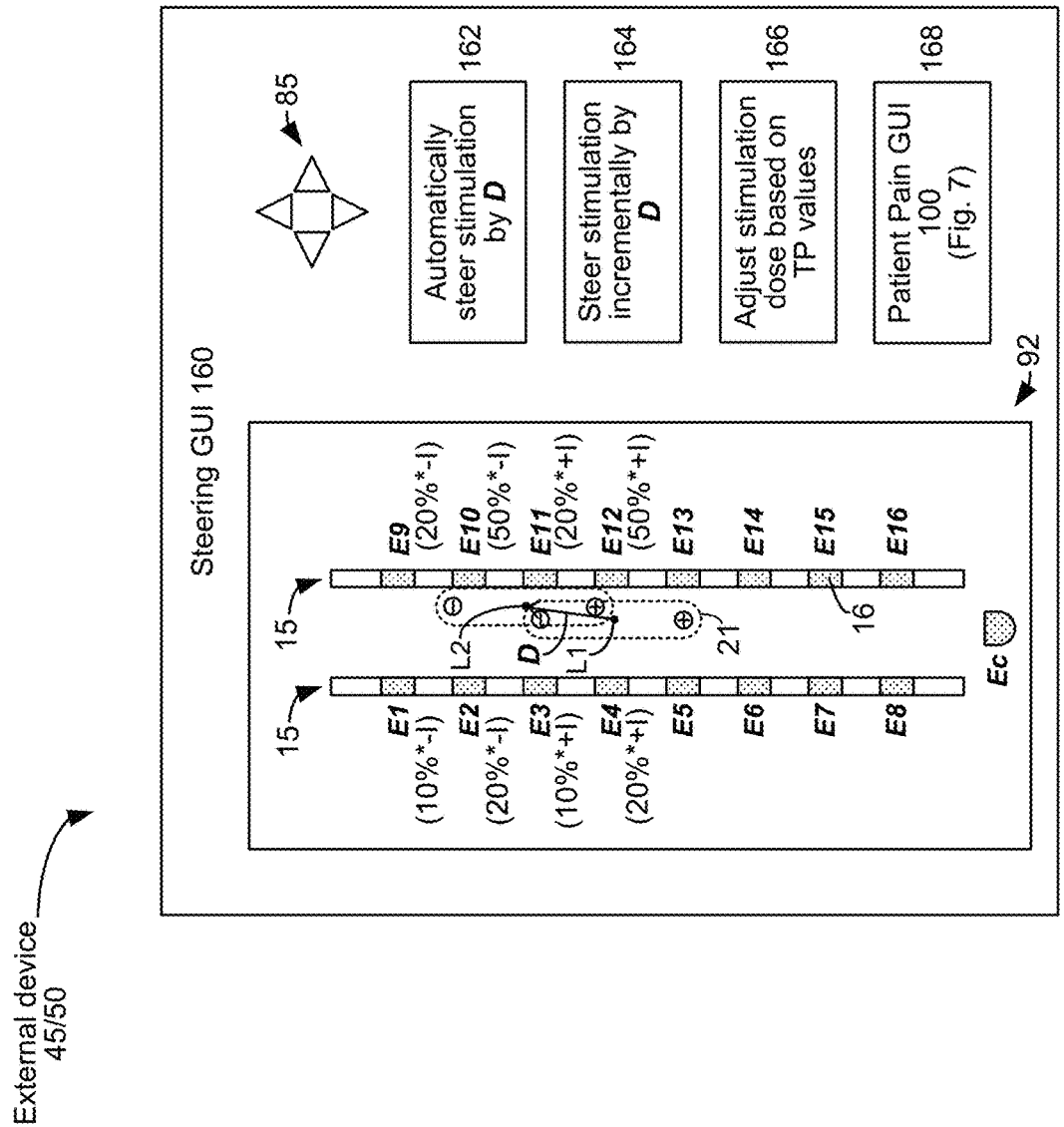
FIG. 10 shows a steering GUI which may be used by the patient to move stimulation in the electrode array in accordance with the steering vector D.

Once steering vector D has been defined using the TP values, stimulation can be moved to a new location in the electrode array (L2) in accordance with vector D in step 214. Again, this can occur in different ways, and can be assisted by the GUI of the external device being used. For example, and returning to FIG. 7, after the patient has populated metrics in the patient pain GUI 100, and once TP values and steering vector D are determined by the steering algorithm 200, the patient may select an option 101 to allow the patient to enter a steering mode to move the stimulation. Selection of this option 101 can cause the external device to display a steering GUI 160 as shown in FIG. 10. FIG. 10 shows in the leads interface 92, including the present location of stimulation (L1) and a new location (L2) to which stimulation can be moved in accordance with steering vector D. The patient could in this example use the directional arrows 85 to incrementally move stimulation from L1 to L2. That being said, this may be overly complicated for a patient or to implement on the patient external controller 45.

Simpler mechanisms for moving the stimulation in accordance with vector D could also be used in steering GUI 160. For example, an option 162 may allow the patient to automatically move the stimulation by vector D to new location L2. Notice that moving the stimulation will cause the electrode configuration (the active electrodes, and their polarities and relative percentages % X) to change, as dictated by operation of the electrode configuration algorithm described earlier and discussed in U.S. Pat. No. 10,881,859. As shown in FIG. 10 for example, moving the stimulation to new location L2 moves the poles (anode + and cathode −) in the pole configuration 21 up and to the right per vector D. Because this brings the cathode pole in the pole configuration closest to electrode E10, the electrode configuration algorithm will assign this electrode the largest percentage (e.g., 50%) of the cathodic current (−I). Electrodes E2, E9 and E1, which are further away from the cathode pole, will receive smaller percentages (e.g., 20%, 20% and 10% respectively) to position the cathode pole at its prescribed location per vector D. The anode pole is also moved up and to the right, with the anodic current (+I) being shared between electrodes E3, E4, E11, and E12 per the electrode configuration algorithm, which positions the anode pole at its new location per vector D.

After stimulation is moved, it may be warranted to adjust certain simulation parameters, as shown in optional step 216. This is especially true as concerns amplitude: if the new stimulation location L2 involves the activation of electrodes that are for example closer to the spinal cord, it may be reasonable to decrease the amplitude of the stimulation. Automatic stimulation adjustments may be made as well, and in particular adjustments to the neural dose provided by the stimulation may occur at optional step 217, although this is discussed later with reference to FIG. 11.

Moving the stimulation directly from L1 to L2 using GUI option 162 (FIG. 10) may comprise too sudden a change to the patient's stimulation, which may be uncomfortable for the patient. As such, another option 164 when selected will move the stimulation an incremental amount (e.g., 0.1 mm) from location L1 towards L2 in the direction prescribed by steering vector D. In other words, selection of option 164 doesn't move the stimulation the full magnitude prescribed by steering vector D. Instead, the patient may select option 164 numerous times to fully move the stimulation the full magnitude. The examples in FIG. 10 describing how stimulation can be moved in accordance with steering vector D are merely examples, and other examples are possible.

Once stimulation has been moved, the steering operation can iterate or repeat, as shown in step 218. This may comprise a selectable option 168 in steering GUI 160, which returns the patient to the patient pain GUI 100 shown in FIG. 7. At this point, the patient may again enter pain scores and percentage coverages for each of the body regions; TP values and a new steering vector D can be determined; thus allowing the patient to again move stimulation in an attempt to more precisely target their pain. It should be understood that more precise targeting would generally reflect a lowering of the computed TP values at all body regions of relevance.

As discussed earlier with reference to step 216, it can be prudent to adjust stimulation parameters after the location of stimulation is moved. As part of stimulation parameter adjustment, the steering algorithm 200 may more specifically adjust the neural dose of the stimulation in step 217. Neural dose refers to the mean charge per second that the IPG or ETS delivers to the patient's tissue. Generally speaking, the neural dose scales with the product of the current amplitude (I), the pulse width (PW), and the frequency (F). The neural dose generally affects the power that the stimulation device must deliver, and hence impacts the power that the battery in the device (e.g., 14, FIG. 1) must deliver. If the neural dose is higher, the battery 14 must deliver more power. Thus, at higher neural doses, the battery 14 if rechargeable will need to be recharged more frequently, or if permanent will need to be replaced more frequently, as discussed in PCT (Int'l) Patent Application Publication 2021/178105, which is incorporated herein by reference in its entirety. As a result, it is preferred that the neural dose delivered by the IPG or ETS be as low as possible.

The TP values determined by the steering algorithm 200 can be relevant to determining the neural dose the patient should receive at step 217, because these TP values may be indicative of neural dose required for effective pain relief. Assume for example that the steering algorithm 200, even after some iterations, has caused the patient to steer the stimulation to an optimal location in the electrode array 17.

Assume further that while this location is optimal, the patient's TP values in the respective body regions Ri are still rather poor (high). For example, the average of the TP values of the various body regions R—AVG(TP(R))—may be relatively poor (high), and/or the TP values have a high variance—STD(TP(R)). In either case, the stimulation, even though optimally located in the electrode array 17, does not precisely target the patient's pain in all affected body regions Ri.

If the TP values reflect that the stimulation is not precisely targeting the patient's pain uniformly across all body regions (e.g., the average and/or standard deviation is high), this may suggest that it is prudent to increase the neural dose of the stimulation that the patient will receive at step 217, because higher neural doses are likely to address the lack of the precision. Increasing the neural dose can comprise increasing any one or more of I, PW, or F. While increasing the neural dose would increase power draw in the IPG or ETS, and thus potentially stress that device's battery, this outcome may be unavoidable to provide effective stimulation for the patient. Similarly, if the TP values reflect that the stimulation is precisely targeting the patient's pain uniformly across all body regions (e.g., the average and/or standard deviation is low), this may suggest that it is prudent to decrease the neural dose of the stimulation that the patient will receive at step 217. This may be desirable because decreasing the neural dose would decrease power draw in the IPG or ETS, and thus reducing the stress that's device's battery. Again, lowering the neural dose can comprise lowering any one or more of I, PW, or F.

Figure 11:
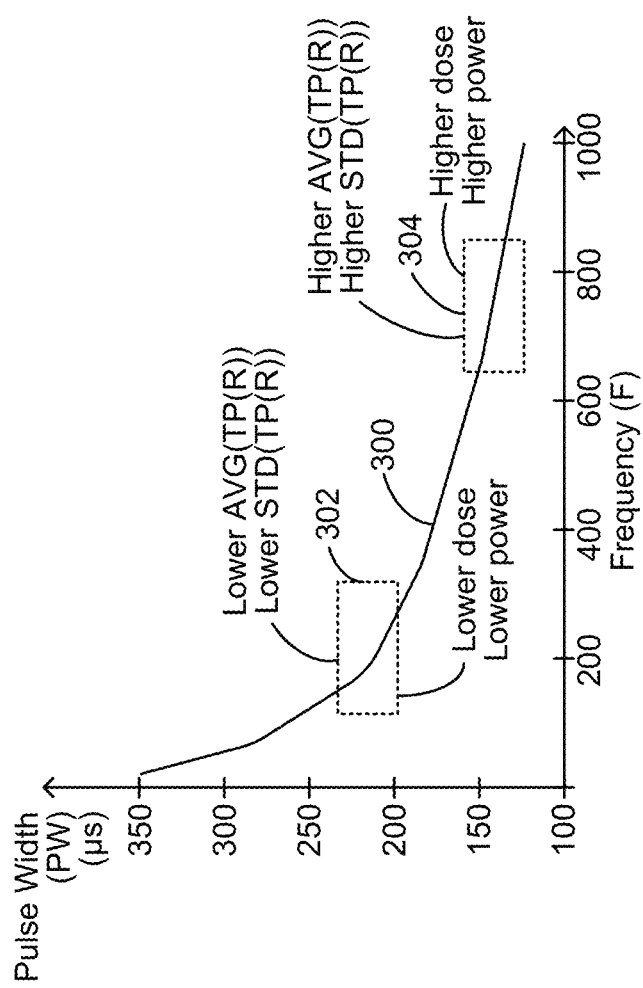
FIG. 11 shows optionally how a neural dose of the stimulation can be varied in accordance with the TP values.

FIG. 11 shows an example of how adjusting the neural dose can occur at step 217 in accordance with a neural dose model 300. This neural dose model 300 is taken from the above-referenced '105 Publication, which provides a relationship between frequencies and pulse widths that provide effective stimulation, in particular when the stimulation is provided at a level the patient cannot feel—i.e., sub-perception stimulation not accompanied by paresthesia. Generally speaking, lower neural doses are provided at lower frequencies in model 300, while higher neural doses are provided at higher frequencies. Thus, if the patient is not well targeted per their TP values, the neural dose can be increased by increasing the frequency of the stimulation (and adjusting the PW accordingly per model 300), such as by selecting stimulation parameters appearing in portion 304 of the model 300. In this example, the amplitude I of the stimulation may remain unchanged, although it could also be increased to (further) increase the neural dose. Likewise, if the patient is well targeted per their TP values, the neural dose can be decreased by decreasing the frequency of the stimulation (and adjusting the PW accordingly per model 300), such as by selecting stimulation parameters appearing in portion 302 of the model 300. In this example, the amplitude I of the stimulation may again remain unchanged, although it could also be decreased to (further) decrease the neural dose. Again, decreasing the neural dose may be prudent to reduce stress on the battery, and may also be prudent to prevent over-stimulating the patient. It should be understood that model 300 is merely one example that could be used by the algorithm 200 to provide automatic adjustment of stimulation parameters based on calculated TP values.

One skilled will understand that aspect of steering algorithm 100 described herein can be formulated and stored as instructions in a computer-readable media, such as in a magnetic, optical, or solid state memory. The computer-readable media with such stored instructions may reside with a relevant external device, such as the external controller 45 or clinician programmer 50, in a memory stick used to transmit information to such devices, or in the IPG 10 or ETS 40. The computer-readable media may also reside in a server or any other computer device, thus allowing instructions to be downloaded to these stimulator system devices, via the Internet for example.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method implementable using an external device in communication with a stimulator device having a plurality of electrodes forming an electrode array, the method comprising:
providing stimulation at a first location in the electrode array;
receiving at a user interface of the external device a plurality of inputs for each of a plurality of body regions, wherein the plurality of inputs are indicative of how well the stimulation at the first location is targeting the patient's symptoms, wherein one of the plurality of inputs comprises a pain score;
computing a value for each of the body regions using the plurality of inputs for each body region;
determining using the values at least a direction from the first location in which the stimulation can be moved in the electrode array to better target the patient's symptoms; and
programming the stimulator device to move the stimulation to a second location in the electrode array in accordance with the direction.

2. The method of claim 1, wherein the value for each of the body regions is computed using the external device.

3. The method of claim 1, wherein the at least the direction is determined using the external device.

4. The method of claim 1, wherein the stimulator device is programmed to move the stimulation using the user interface of the external device.

5. The method of claim 1, wherein the external device comprises a hand-held portable patient external controller.

6. The method of claim 1, wherein the plurality of inputs for each of the body regions further comprises an indication of stimulation coverage.

7. The method of claim 6, wherein the value for each of the body regions is computed using a model having the pain score and the indication of stimulation coverage as inputs.

8. The method of claim 1, wherein a direction and distance from the first location in which the stimulation can be moved is determined using the values.

9. The method of claim 8, wherein the stimulator device is programmed to move the stimulation in the electrode array in accordance with the direction and the distance.

10. The method of claim 1, wherein the direction is determined by computing a gradient of the values over x and y dimensions.

11. The method of claim 10, wherein the direction is determined in accordance with a highest computed gradient.

12. The method of claim 1, further comprising adjusting at least one stimulation parameter of the stimulation after it is moved to the second location.

13. The method of claim 12, wherein the at least one stimulation parameter comprises an amplitude of the stimulation.

14. The method of claim 12, wherein the at least one stimulation parameter is adjusted in accordance with the values.

15. The method of claim 14, wherein the at least one stimulation parameter is adjusted in accordance with one or more of an average of the values or a deviation of the values.

16. The method of claim 15, wherein the at least one stimulation parameter is adjusted to increase a neural dose of the stimulation if the average of the values or the deviation of the values is high, or wherein the at least one stimulation parameter is adjusted to decrease the neural dose of the stimulation if the average of the values or the deviation of the values is low.

17. A system, comprising:
an external device for communicating with a stimulator device having a plurality of electrodes forming an electrode array, the external device comprising:
a user interface; and
controller circuitry programmed with an algorithm, wherein the algorithm is configured to:
program the stimulation device to provide stimulation at a first location in the electrode array;
receive from the user interface a plurality of inputs for each of a plurality of body regions, wherein the plurality of inputs are indicative of how well the stimulation at the first location is targeting the patient's symptoms, wherein one of the plurality of inputs comprises a pain score;
compute a value for each of the body regions using the plurality of inputs for each body region;
determine using the values at least a direction from the first location in which the stimulation can be moved in the electrode array to better target the patient's symptoms; and
program the stimulator device to move the stimulation to a second location in the electrode array in accordance with the direction.

18. A non-transitory computer readable medium comprising instructions executable on an external device for controlling a stimulator device that provides stimulation to a patient, wherein the instructions when executed enable the external device to:
program the stimulation device to provide stimulation at a first location in the electrode array;
receive from the user interface a plurality of inputs for each of a plurality of body regions, wherein the plurality of inputs are indicative of how well the stimulation at the first location is targeting the patient's symptoms, wherein one of the plurality of inputs comprises a pain score;
compute a value for each of the body regions using the plurality of inputs for each body region;
determine using the values at least a direction from the first location in which the stimulation can be moved in the electrode array to better target the patient's symptoms; and
program the stimulator device to move the stimulation to a second location in the electrode array in accordance with the direction.

* * * * *